United States Patent
Krellmann et al.

(10) Patent No.: US 8,400,150 B2
(45) Date of Patent: Mar. 19, 2013

(54) MAGNETIC RESONANCE SYSTEM AND METHOD FOR CONTROL THEREOF

(75) Inventors: Christof Krellmann, Erlangen (DE); Stefan Assmann, Erlangen (DE); Andrea Hopf, Gaal (AT); Mike Mueller, Moehrendorf (DE); Michaela Schmidt, Uttenreuth (DE); Peter Speier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 434 days.

(21) Appl. No.: 12/698,292

(22) Filed: Feb. 2, 2010

(65) Prior Publication Data

US 2010/0198373 A1 Aug. 5, 2010

(30) Foreign Application Priority Data

Feb. 2, 2009 (DE) .......................... 10 2009 007 045

(51) Int. Cl.
*G01V 3/00* (2006.01)

(52) U.S. Cl. ........................................ 324/309; 324/307
(58) Field of Classification Search ................. 324/309, 324/307, 306, 300
See application file for complete search history.

(56) References Cited

U.S. PATENT DOCUMENTS

| | | | | |
|---|---|---|---|---|
| 5,512,826 A * | 4/1996 | Hardy et al. | .................. | 324/309 |
| 6,166,544 A * | 12/2000 | Debbins et al. | ............... | 324/309 |
| 6,275,721 B1 * | 8/2001 | Darrow et al. | ................ | 600/410 |
| 6,801,037 B1 * | 10/2004 | Zhang | .......................... | 324/309 |
| 6,963,768 B2 * | 11/2005 | Ho et al. | ....................... | 600/415 |
| 7,020,844 B2 | 3/2006 | Trevino et al. | | |

* cited by examiner

*Primary Examiner* — Louis Arana
(74) *Attorney, Agent, or Firm* — Schiff Hardin LLP

(57) ABSTRACT

A method to control a magnetic resonance system includes at least one protocol step for measurement data acquisition with the magnetic resonance system, and at least one operator interaction step which allows an operator to enter information that affects at least one subsequent step in the control of the magnetic resonance system.

8 Claims, 2 Drawing Sheets

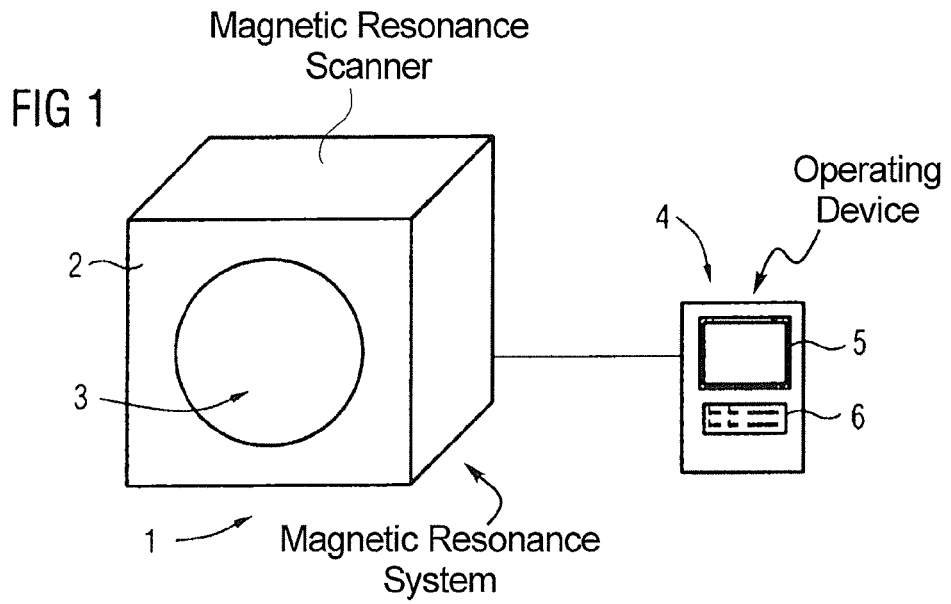
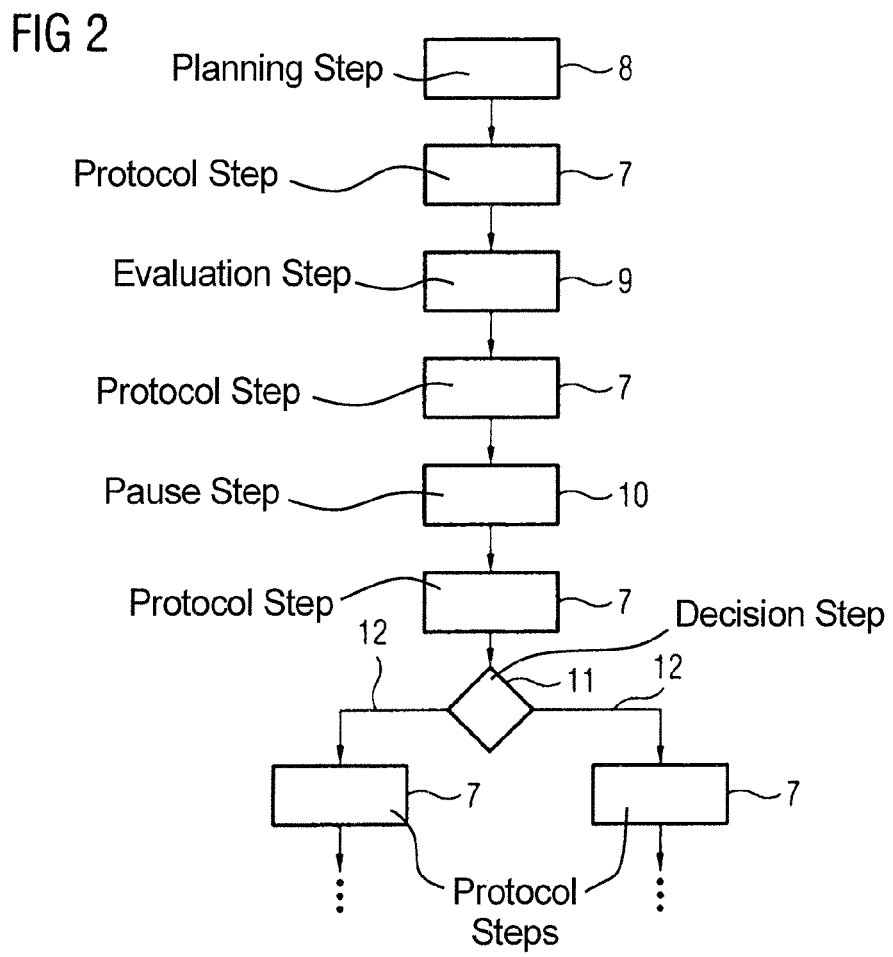

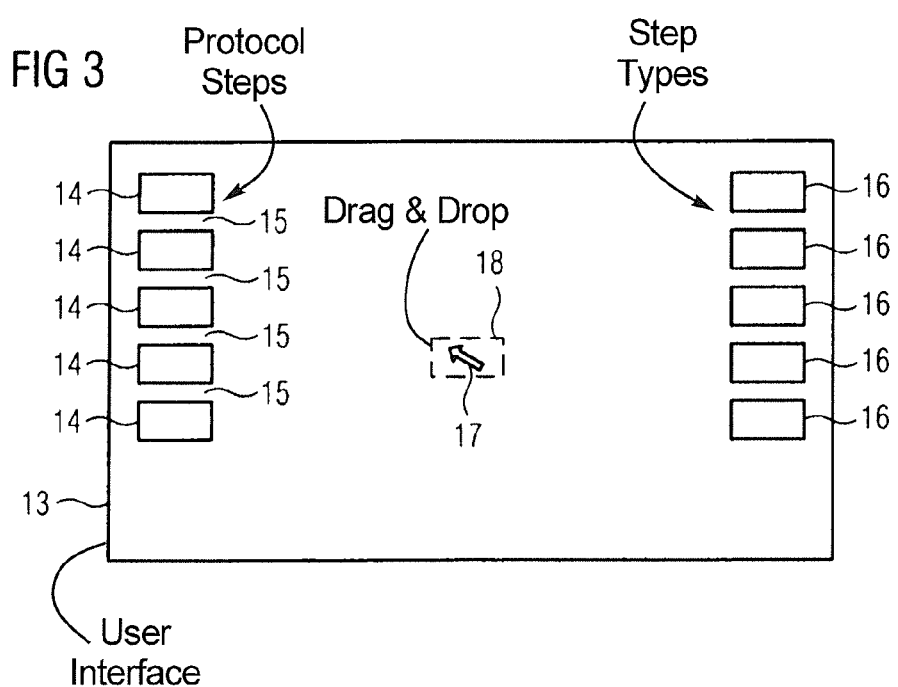

MAGNETIC RESONANCE SYSTEM AND METHOD FOR CONTROL THEREOF

BACKGROUND OF THE INVENTION

1. Field of the Invention

The present invention concerns a method to control a magnetic resonance system, of the type having at least one protocol step for measurement data acquisition with the magnetic resonance system according to a measurement protocol, as well as a magnetic resonance system to execute such a method.

2. Description of the Prior Art

Control methods (frequently also designated as measurement programs) of the general type noted above are known and serve to implement an examination of a patient with a magnetic resonance system as optimally as possible. Such measurement programs (also known as organ programs, for example) are largely executed automatically without users being able to input additional information.

The core of such control methods are program steps that describe measurement tasks that are executed successively by the magnetic resonance system, meaning that measurement data representing magnetic resonance images are acquired. Each of these protocol steps is planned independently in advance. The possibility to insert pause steps (in which contrast agent can be administered, for example) into the method workflow is known. Pop-up windows can be provided that contain an appropriate instruction to the operator, and the operator can then end the pause by a confirmation button or the like. The pop-up windows are superimposed on an operating screen of the magnetic resonance system. The next protocol step is subsequently executed with the next measurement protocol.

This means that control methods known today for magnetic resonance systems are quite rigid in their workflow as it was defined initially. If an operator would like to adapt the method workflow or individual protocol steps—for example based on specific patient properties or observations—the method workflow must be interrupted and the changes must be implemented individually for every protocol step, thus through the steps "Open", "Edit", "Close". It can thereby also be necessary to make the same adjustments multiple times.

If, during the examination, evaluations of the images are made—for example marking of regions of interest—the examination mask must be exited. The measurement data on which the evaluation should be conducted must be loaded onto another operating device or into another user interface so that the corresponding evaluation application can be opened. When the evaluation is terminated, the operator returns with the result to the examination and plans the further continuation of the examination based on this evaluation for every protocol step.

This conventional procedure is very laborious and inflexible and requires a high time outlay from the operator. Faulty measurements and operating errors can additionally occur since a user can overlook manual operating steps.

SUMMARY OF THE INVENTION

An object of the present invention is to provide a method to control a magnetic resonance system that is improved with regard to user friendliness and flexibility.

To achieve this object, in a method of the aforementioned type, at least one operating interaction step is provided according to the invention that allows an operator to enter (input) information in the method workflow.

The operating interaction is incorporated as a component of the control method in the method workflow so that an improved user direction can be conducted by the examination to be implemented. In contrast to a pause step with a measurement pause that can be ended by the operator, which naturally also can be an additional part of the method according to the invention, the operating interaction step is characterized by allowing information to be input that actually affects the further (subsequent) workflow of the control method. It is thus no longer necessary for the operator to exit the examination; rather, modifications can be integrated into the ongoing examination workflow. Moreover, possible operating errors are also reduced since the operator cannot forget that possible additional manual operating steps must be taken.

The operating interaction step can be at least one planning step for adjustment by the operator of acquisition parameters of at least one following protocol step and/or at least one evaluation step to evaluate measurement data acquired in a preceding protocol step using an evaluation algorithm, and for adjustment by the operator of acquisition parameters of at least one following protocol step depending on the evaluation result and/or at least one decision step for a decision by the operator about the further method workflow, in particular for the selection of at least one method segment including at least one additional protocol step.

The above examples for operating interaction steps represent in more detail the manner in which situations an operator interaction can occur in the method according to the invention. A planning step serves for the planning of at least one following protocol step in the workflow of the control method itself. Acquisition parameters defined in a planning step for at least two following protocol steps (preferably for all following protocol steps) can be adopted. For example, in this embodiment it is possible not only to produce a plan for a single protocol step but also to set information (thus acquisition parameters) that then in particular is valid for the entire further method workflow. This means that the acquisition parameters are stored and later used by the required protocol steps. A planning step thus can require the operator to plan the slices for all following measurements, for example on a user interface. The operator does this and confirms the positioning. In the following steps the stored information of the slice planning can be retrieved again. Another example of the usage of planning steps is the possibility of short-term consideration of additional patient properties. For example, if it is established that the patient is not in the position to hold his breath given selection of a protocol that provides a breath-hold of the patient, this can be communicated to the control method and said control method can be correspondingly adapted, for example in that an acquisition technique is used that manages without a breath-hold.

Furthermore, it is possible to use at least one evaluation step. In an evaluation step that represents a portion of the control method, an evaluation algorithm can be applied to already-acquired measurement data. The operator can possibly also select which evaluation algorithm he would like to apply to which measurement data. The evaluation result is displayed to the operator so that said operator can adjust or even modify corresponding acquisition parameters that affect the subsequent protocol steps. In this case it is also possible for acquisition parameters, defined in an evaluation step for at least two following protocol steps (in particular all following protocol steps) to be adopted. The advantage also results (as in the planning step) that inputs do not need to be laboriously implemented for all protocol steps, such that the effort is reduced and the user friendliness is improved. For example, in an evaluation step a region of interest can be marked, whereupon an intensity-time curve can be calculated and displayed from the measurement data/magnetic resonance images acquired beforehand. Based on this, at least one subsequent protocol step can be planned in the method workflow. Given a measurement with contrast agents, another example would be to initially inject a test bolus, to evaluate the measurement data and then to make an adaptation or to adopt these contrast agent parameters.

The aforementioned decision step is another advantageous example of an operating interaction step. In such a decision step the operator can make adjustments at a specific point in the control method, which adjustments can affect the further method workflow. These adjustments are then for the most part based on a visual evaluation of already-acquired measurement data, which means that it can be provided that the already-acquired magnetic resonance images are always displayed at the decision step (which necessarily requires a pause). If the operator now recognizes a circumstance indicating plaque in the carotid, he can choose whether the method is continued with a plaque program or flow measurements in order to acquire additional information via the examination. Another example is the detection of a tumor, wherein the following method workflow can, for example, be selected differently depending on the tumor type. It is noted that, for example, acquisition parameters can also be adapted in a decision step. As already described, such adaptations can also advantageously apply for all following protocol steps.

Overall, in this embodiment the method according to the invention thus enables the method elements of protocol step and pause step that are provided in the prior art to be expanded with additional elements, for example here planning step, evaluation step and decision step. Like the pause step, these steps do not trigger a measurement but require an operator interaction. The activities of planning, evaluation and deciding are integrated into the examination workflow so that time is saved and the focus is kept on the examination itself.

In a further embodiment of the method according to the invention at least one planning step and/or at least one evaluation step and/or at least one decision step are inserted, defined by the operator, into a predefined method workflow. Even if a predefined program (for example an organ program) has been selected for an examination, it is possible for the operator to insert operator interaction steps at points that he has established in the method workflow. For example, this can occur via a user interface in which the additional elements of pause step, planning step, evaluation step and decision step can simply be added into the method workflow. In this way a user can flexibly adapt the measurement program so that an optimal user direction is provided.

In addition to the method, the present invention also concerns a magnetic resonance system fashioned to implement the method according to the invention. This accordingly offers an improved operating concept which, in addition to enabling a better user direction, also reduces operating errors.

BRIEF DESCRIPTION OF THE DRAWINGS

FIG. 1 schematically illustrates a magnetic resonance system according to the invention.

FIG. 2 is a flowchart of an embodiment of the method according to the invention.

FIG. 3 shows an example of a user interface for the adaptation of the method workflow in accordance with the invention.

DESCRIPTION OF THE PREFERRED EMBODIMENTS

FIG. 1 shows a magnetic resonance system 1 according to the invention. The system 1 has a scanner 2 (basic field magnet) in which a patient can be inserted through a patient receptacle 3. The design of the scanner 2 with gradient coils, radio-frequency coils and the like is generally known and need not be described in further detail herein.

The magnetic resonance system 1 also has an operating device 4 with a display device 5 and an input device 6 via which the control of the magnetic resonance system 1 ensues. The magnetic resonance system 1 is fashioned to implement the method according to the invention, as explained in detail in the following with reference to FIG. 2.

FIG. 2 shows a flowchart of an embodiment of the method according to the invention. The present example of a method according to the invention—which naturally is not limited with regard to its steps—includes a number of protocol steps 7, a planning step 8, an evaluation step 9, a pause step 10 and a decision step 11, These elements (protocol step 7, planning step 8, evaluation step 9, pause step 10, decision step 11) form the basic components of every control method according to the invention and can ultimately occur in arbitrary numbers. The planning step 8, the evaluation step 9 and the decision step 11 require the operator to input information that can affect the further method workflow. This is explained in detail using the example shown in FIG. 2.

First, acquisition parameters that can be valid for specific following protocol steps 7—however in particular can also be valid for more than one, preferably all, protocol steps 7—are defined directly or indirectly by the operator in planning step 8. The entire measurement process that is composed of different measurements in the protocol steps 7 thus can be planned in a simple manner in the planning step 8.

A first acquisition of measurement data according to a measurement protocol and the acquisition parameters (defined in particular in Step 8) then ensues in Step 7. Such an acquisition of measurement data ensues in every protocol step 7. The measurement data describe magnetic resonance images that are to be evaluated later. Presently a measurement with a test bolus should now be implemented first in first protocol step 7.

In the evaluation step 9 the measurement data of the preceding protocol step 7 are now evaluated with an evaluation algorithm, whereupon the evaluation result is presented to an operator at the display device 5. This operator assesses the evaluation result and can thereupon define and/or adapt acquisition parameters. As already is the case in planning step 8, these apply not only for the next protocol step 7 but also beyond this. For example, the injection scheme for the contrast agent can now be adapted.

Additional measurement data are now acquired in protocol step 7 following the evaluation step 7. A pause step 10 follows this in which new contrast agent is injected and the conducted injection is then confirmed by the operator. An additional measurement data acquisition can then ensue in a third protocol step 7.

In decision step 11 the acquired magnetic resonance images that are reconstructed from the measurement data are then displayed to the operator. Based on these displayed images the operator can now decide how the examination should proceed further. For example, if a tumor is detected, different additional method steps can be reasonable for a benign tumor than for a malignant tumor. This is indicated in the present example by the protocol steps 7 following the arrows 12.

Planning, evaluation and deciding are thus incorporated in this way into the control method during the examination, such that the user friendliness increases significantly.

Within the scope of the method according to the invention it is also possible for an operator to insert operator interaction steps or pause steps into the method workflow in advance. For example, this can ensue via a user interface 13 as it is shown in FIG. 3. There method steps 14 with intervening spaces 15 are shown to the left. Different step types 16 can be selected on the right side—for example by means of a cursor 17—and can be moved into the intervening spaces 15 by a drag-and-drop procedure, as is indicated by the box 18 drawn in dashed lines.

The operator can thus arbitrarily adapt the method workflow to his or her requirements.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for controlling a magnetic resonance system, comprising:
    in order to execute a data acquisition procedure to acquire magnetic resonance data from a subject in a magnetic resonance data acquisition unit from a control unit connected to the magnetic resonance data acquisition unit, entering, via a user interface in communication with said control unit, at least one operating protocol that defines a plurality of successive protocol steps that forms said data acquisition procedure;
    in said at least one operating protocol, including at least one operator interaction step that is then built into said at least one operating protocol to occur at a predetermined time, among said plurality of successive protocol steps, during execution of said data acquisition procedure;
    beginning execution of said data acquisition procedure from said control unit by operating the magnetic resonance data acquisition unit according to said operating protocol;
    when said operator interaction step occurs in said operating protocol, interrupting said execution of said data acquisition protocol and displaying, at said user interface, at least one operator interaction field allowing an operator to make an entry in said operator interaction field that affects subsequent protocol steps in said operating protocol; and
    after said operator makes said entry in said operator interaction step, controlling protocol steps in said operating protocol, that occur subsequent to said operator interaction step, from said control unit dependent on said entry.

2. A method as claimed in claim 1 wherein said operator interaction step comprises a planning step that allows, as said entry in said operator interaction field, an adjustment of data acquisition parameters in at least one of said protocol steps following said planning step.

3. A method as claimed in claim 1 wherein said operator interaction step comprises an evaluation step that allows, as said entry in said operator interaction field, an evaluation algorithm to be initiated by an operator to evaluate measurement data acquired in at least one of said protocol steps preceding said evaluation step to obtain an evaluation result, and to allow adjustment by the operator of data acquisition parameters for at least one of said protocol steps following said evaluation step, dependent on said evaluation result.

4. A method as claimed in claim 1 wherein said operator interaction step comprises a decision step allowing, as said entry in said operator interaction field, entry of an indication representing a decision by an operator with respect to said further execution of said procedure.

5. A method as claimed in claim 4 wherein said decision step comprises allowing the operator to add at least one additional protocol step to said plurality of protocol steps.

6. A method as claimed in claim 1 comprising allowing an operator to freely insert said operator interaction step, via said user interface, between any successive two of said protocol steps after entering said operator protocol into said control unit.

7. A method as claimed in claim 6 comprising, in addition to insertion of said operator interaction step, allowing an operator to insert a pause step in said data acquisition procedure.

8. A method as claimed in claim 1 comprising embodying said at least one user interaction step in said at least one operating protocol before entry of said at least one operating protocol into said control unit.

* * * * *